Figure 1:
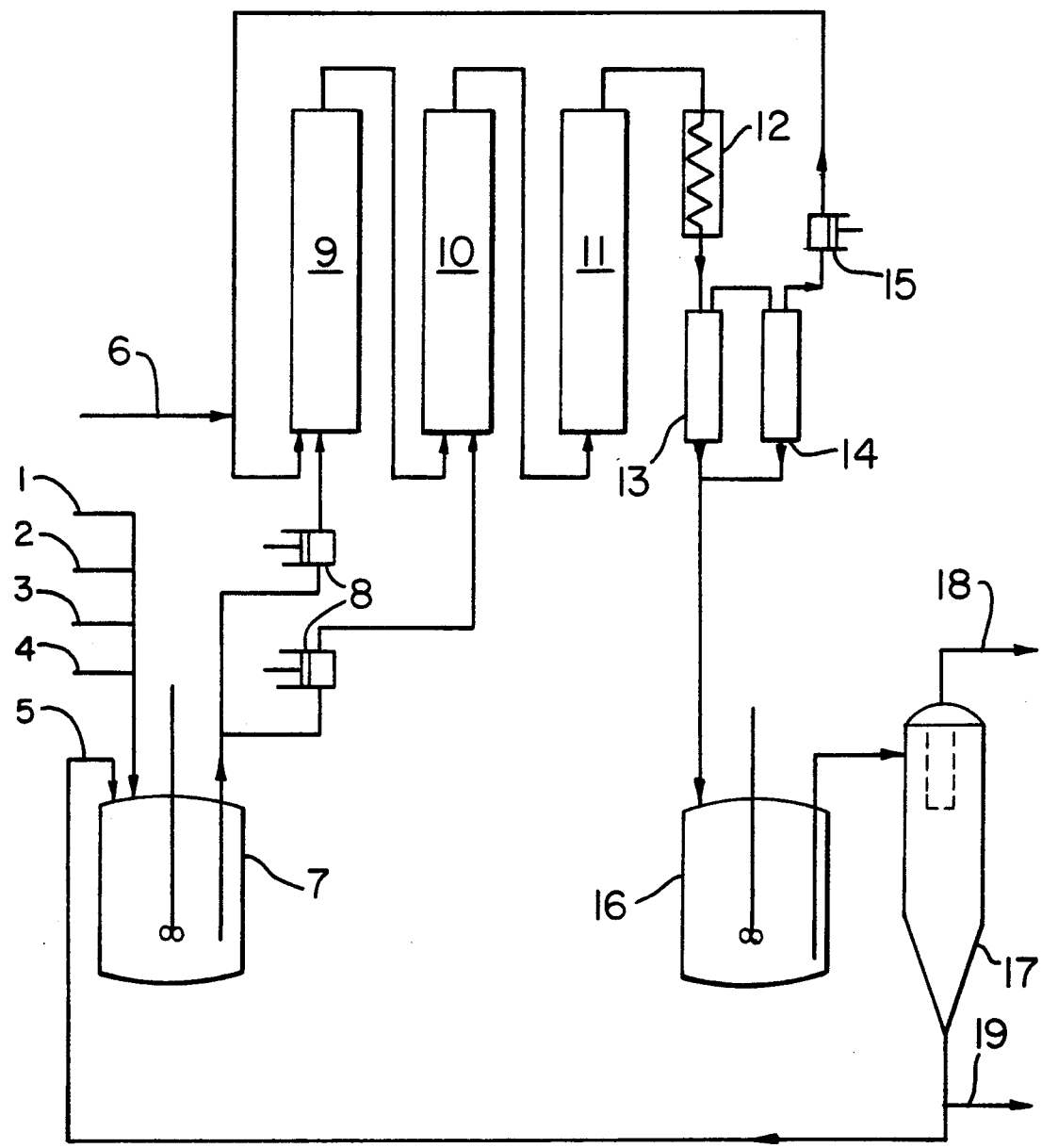

United States Patent [19]

Birkenstock et al.

[11] Patent Number: 5,120,875
[45] Date of Patent: Jun. 9, 1992

[54] PROCESS FOR THE PREPARATION OF CHLORINE-SUBSTITUTED AROMATIC AMINES

[75] Inventors: Udo Birkenstock, Ratingen; Ulrich Kappler, Langenfeld; Herbert Schmidt; Jürgen Zander, both of Leverkusen, all of Fed. Rep. of Germany

[73] Assignee: Bayer Aktiengesellschaft, Leverkusen, Fed. Rep. of Germany

[21] Appl. No.: 566,593

[22] Filed: Aug. 13, 1990

[30] Foreign Application Priority Data

Aug. 26, 1989 [DE] Fed. Rep. of Germany ....... 3928329

[51] Int. Cl.$^5$ ............................................ C07C 209/36
[52] U.S. Cl. .................................... 564/417; 564/442
[58] Field of Search ................................. 564/417, 442

[56] References Cited

U.S. PATENT DOCUMENTS

| | | | |
|---|---|---|---|
| 3,145,231 | 8/1954 | Kosak | 564/417 |
| 3,328,465 | 6/1967 | Spiegler | 564/417 |
| 3,546,297 | 12/1970 | Kosak | 564/417 |
| 4,070,401 | 1/1978 | Hirai et al. | 564/417 |
| 4,230,637 | 10/1980 | Zander | 564/417 |

FOREIGN PATENT DOCUMENTS 0073105 3/1983 European Pat. Off. .
2743610 3/1979 Fed. Rep. of Germany .

OTHER PUBLICATIONS

Rose et al., *The Condensed Chemical Dictionary*, p. 22 (1965).

*Primary Examiner*—Glennon H. Hollrah
*Assistant Examiner*—Scott C. Rand
*Attorney, Agent, or Firm*—Sprung Horn Kramer & Woods

[57] ABSTRACT

In the preparation of chlorinated aromatic amines by reaction of corresponding nitro compounds with hydrogen under pressure, at elevated temperature and in the presence of a solvent and small amounts of a basic compound, fewer by-products are formed by using platinum and nickel and/or cobalt on an active charcoal support.

7 Claims, 1 Drawing Sheet

PROCESS FOR THE PREPARATION OF CHLORINE-SUBSTITUTED AROMATIC AMINES

The present invention relates to an improved process for the preparation of chlorine-substituted aromatic amines.

It is known that chlorine-substituted aromatic amines can be prepared by hydrogenation of the corresponding nitro compounds in the presence of noble metal catalysts (see Ullmann, Volume 7, 4th edition, page 570 (1973)). It is furthermore known that the undesirable dehydrohalogenation reactions during this hydrogenation can be largely suppressed by using noble metal catalyst systems having a selective action, for example palladium and ruthenium on support materials (see EP-OS (European Published Specification) 0,073,105 and U.S. Pat. No. 4,760,187), or by additions of basic compounds, for example ammonia or morpholine (see DE-OS (German Published Specification) 2,743,610, U.S. Pat. Nos. 3,145,231, 3,361,819 and 3,291,832), or by partial poisoning of catalysts (see U.S. Pat. No. 4,059,627).

It is furthermore known that the activity and selectivity of noble metal catalysts can be influenced by additives. Thus, according to U.S. Pat. No. 3,253,039, the activity of platinum catalysts is improved by addition of silver, whereas chromium and nickel have a poisoning effect on the catalyst.

According to U.S. Pat. No. 2,823,235, nickel catalysts lead to the formation of azo-, azoxy- and hydroazobenzenes during hydrogenation of nitrobenzene, and according to U.S. Pat. No. 3,145,231 they intensify the dehydrohalogenation. U.S. Pat. No. 3,546,297 states that only a combination of $Cr^{3+}$ and $Ni^{2+}$ compounds as additives to platinum catalysts causes an increase in catalyst activity without a simultaneous increase in the rate of dehydrohalogenation, whereas $Cr^{3+}$ or $Ni^{2+}$ compounds by themselves are in each case ineffective. According to EP-OS (European Published Specification) 0,073,105 and U.S. Pat. No. 4,760,187, the formation of the undesirable by-product 3,3',4,4'-tetrachloroazobenzene (TCAB) is significantly promoted by using platinum catalysts which contain additions of $Cr^{3+}$ and $Ni^{2+}$ compounds in the hydrogenation of 3,4-dichloronitrobenzene.

If dehydrohalogenation inhibitors, for example morpholine, are used, according to U.S. Pat. No. 3,291,032 as a rule an increased TCAB content must likewise be accepted in 3,4-dichloroaniline prepared by hydrogenation of 3,4-dichloronitrobenzene. Since TCAB and 3,3',4,4'-tetrachloroazoxybenzene (TCAOB) are known to have dioxin-like properties (Pergamon Series on Environmental Science, Volume 5, pages 534–544; J. Soc. Occup. Med. (1981) 31, pages 158–163 and Science, Volume 194, pages 627–630 (1976)), it is desirable to avoid the formation of TCAB and TCAOB as far as possible.

A process has now been found for the preparation of chlorinated aromatic amines by reaction of chlorinated aromatic nitro compounds of the formula

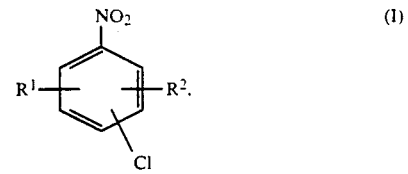

in which

R¹ and R² are identical or different and each denote hydrogen, methyl or chlorine, with hydrogen in the presence of a hydrogenation catalyst under pressure, at elevated temperature and in the presence of a solvent and small amounts of a basic compound, which is characterized in that the reaction is carried out in the presence of platinum and nickel and/or cobalt on an active charcoal support.

Examples which may be mentioned of chlorinated aromatic nitro compounds of the formula (I) are: o-nitrochlorobenzene, m-nitrochlorobenzene, p-nitrochlorobenzene, 2,4-dichloro-nitrobenzene, 2,5-dichloro-nitrobenzene, 3,4-dichloro-nitrobenzene, 2,3,5-trichloro-nitrobenzene, 2,4,6-trichloro-nitrobenzene and 2-chloro-4-nitrotoluene.

Any desired mixtures of chlorinated aromatic nitro compounds of the formula (I) can also be used in the process according to the invention.

3,4-Dichloronitrobenzene is preferably employed.

The process according to the invention can be carried out, for example, at temperatures in the range from 120° to 160° C., preferably 130° to 150° C., under pressures in the range from 50 to 250 bar, preferably 80 to 130 bar.

Examples of possible solvents are: aliphatic alcohols having 1 to 8 C atoms, such as methanol, ethanol, propanol, isopropanol, butanol, isobutanol, pentanol, isopentanol, hexanol and isohexanol (preferably isopropanol), and aromatic hydrocarbons having 6 to 10 C atoms, such as benzene, toluene and xylene (preferably toluene).

Ammonia is preferably employed as the basic compound in the process according to the invention. The ammonia can be employed in gaseous form or as a solution. Possible ammonia solutions are, for example, aqueous solutions or solutions in one of the abovementioned solvents.

The ammonia can be present in the reaction mixture, for example, in an amount of 0.2 to 5% by weight, preferably 0.3 to 3% by weight, particularly preferably 0.7 to 1.5% by weight, based on the chlorinated aromatic nitro compound employed, and if appropriate is to be topped up accordingly in the case of a continuous procedure.

A catalyst on active charcoal as the support material is employed as hydrogenation catalyst in the process according to the invention. The catalyst contains platinum, for example in an amount of 0.3 to 7% by weight, preferably 0.5 to 2% by weight, and nickel and/or cobalt, for example in each case in amounts of 1 to 100% by weight, preferably 10 to 30% by weight, based on the platinum. Catalysts which contain platinum and nickel are particularly preferred.

The active charcoal support for the catalyst can consist of any desired porous or non-porous material. Commercially available porous active charcoals of vegetable or animal origin and having a high surface area are preferably used, such as are obtainable, for example, from the companies Norit, Darco or Degussa.

Such catalysts can be prepared in a manner which is known per se, for example by impregnating an active charcoal support with an aqueous platinum salt solution, for example $H_2PtCl_6$ solution, and if appropriate reducing the salt to the metal with a reducing agent, for example formaldehyde or hydrazine in alkaline solution. The nickel compounds and/or cobalt compounds can be applied to the active charcoal support in various ways. Thus, an aqueous nickel salt solution and/or cobalt salt solution (for example chlorides, nitrates or sulphates) can be added to the active charcoal support containing platinum, nickel compounds and/or cobalt compounds being deposited virtually quantitatively on the active charcoal support under alkaline conditions. Alternatively, the nickel compounds and/or cobalt compounds can also be applied to the active charcoal support together with the platinum compound. Finally, it is also possible to use suitable mixtures of on active charcoal/platinum catalysts, active charcoal/nickel catalysts and/or active charcoal/cobalt catalysts.

The process according to the invention can be operated discontinuously or continuously.

The process according to the invention gives chlorinated aromatic amino compounds of the formula (II)

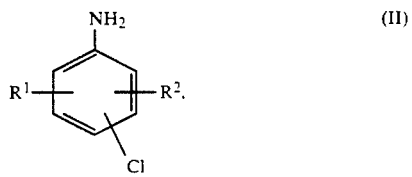

in which

R¹ and R² have the meaning given in the case of formula (I).

For example, o-chloroaniline, m-chloroaniline, p-chloroaniline, 2,4-dichloroaniline, 2,5-dichloroaniline, 3,4-dichloroaniline, 2,3,5-trichloroaniline, 2,4,6-trichloroaniline and 2,4-chlorotoluidine can be prepared in this way.

Such chlorinated aromatic amines are required as intermediate products for the preparation of plant protection agents and dyestuffs.

A decisive advantage of the process according to the invention is that the hydrogenation proceeds very selectively. Dehydrohalogenation reactions take place to only a very low degree and at the same time the formation of by-products of the azobenzene type is also significantly lower than in processes of the prior art. In view of the initially mentioned prior art, this is particularly surprising.

In the process according to the invention it is particularly advantageous that, specifically in the hydrogenation of 3,4-dichloronitrobenzene, the formation of TCAB as a by-product is lower by about one power of ten than in the process described in DE-AS (German Published Specification) 2,743,610.

Expensive post-purification of chlorinated aromatic amines prepared according to the invention, which would otherwise be necessary because of the increased quality requirements, especially in respect of the contents of by-products of the azobenzene type (for example TCAB), can thus be dispensed with.

In the following examples, percentage data are percentages by weight, unless noted otherwise.

EXAMPLE 1

The number references relate to the drawing.

The hydrogenation apparatus used consisted of several tubular reactors (9), (10) and (11) connected in series and provided with cooling tubes to remove the heat of reaction, the product condenser (12), the separators (13) and (14) and the gas circulation pump (15), with the aid of which a hydrogen circulation was produced and maintained.

In a continuous procedure, via feeds (1) to (4), the nitroaromatic to be hydrogenated (1), the solvent (2), freshly added catalyst (3) and if appropriate ammonia (4) were introduced into the kettle (7) and mixed with catalyst (5) recycled in a reaction product/water/solvent mixture.

The mixture was then fed into the reactors (9) and (10) by means of high pressure pumps (8), and in these reactors was reacted with hydrogen (6), which was introduced into reactor (9) together with recycled hydrogen. The heat of reaction was removed with cooling water. The product which left the reactors was cooled in the condenser (12) and separated from the gas phase in the separators (13) and (14). The gas phase was recycled to the reactor (9) by means of the circulation pump (15). The amine solution diverted out of the high pressure chamber via control valves was degassed in the kettle (16) and then freed from the catalyst in the filter (17). The amine solution was sent for working up (18). The catalyst was recycled as a suspension in a reaction product/water/solvent mixture via line (5) to the next hydrogenation batch in the kettle (7). Some of this suspension was removed from the circulation at (19) at a rate corresponding to the addition of fresh catalyst.

3,000 kg of 3,4-dichloronitrobenzene, 4,200 kg of isopropanol/water mixture containing 15% by weight of water and 0.35% by weight of $NH_3$, 0.1 kg of fresh catalyst (1% by weight of platinum and 0.2% by weight of nickel on active charcoal) and 2,000 kg of finished product solution containing 5% by weight of spent catalyst were continuously pumped per hour, as a mixture, into the reactors of the industrial hydrogenation apparatus described above. 1 to 2% of catalyst and 0.1 to 0.2% of ammonia were thus constantly in circulation.

The hydrogen pressure was kept at 100 bar and the reaction temperature was regulated to 140° to 150° C. The product leaving the reactors was free from 3,4-dichloronitrobenzene.

The pH of the solution of 3,4-dichloroaniline (=DCA) prepared was between 9 and 12. The isopropanol/water mixture 85:15 used as the solvent was removed by distillation and re-used without further working up. It contained ammonia. The ammonia consumed was topped up to a content of 0.35% by weight by addition of gaseous ammonia. The crude dichloroaniline separated off after substantial removal of the water of reaction in a separating bottle contained
more than 99% by weight of 3,4-dichloroaniline, less than 50 ppm of 3,3',4,4'-tetrachloroazobenzene (TCAB)
in each case less than 0.3% by weight of monochloroanilines and aniline and
less than 0.1 ppm of 3,3',4,4'-tetrachloroazoxybenzene (TCAOB)
and had a melting point of 71.5° to 71.6° C.

EXAMPLES 2-12

Testing of the catalytic activity of various catalysts was performed by a standardized method of hydrogenation of 3,4-dichloronitrobenzene in the presence of an isopropanol-water mixture and ammonia under pressure in a stirred stainless steel (material No. 1.4580) autoclave which could be heated.

For the testing, 4 g of catalyst were employed for hydrogenation of 100 g of 3,4-dichloronitrobenzene in 300 g of isopropanol/water/mixture containing 15% by weight of water, and 10 ml of aqueous ammonia solution containing 25% by weight of ammonia.

The autoclave was rinsed with hydrogen and brought to a hydrogen pressure of 100 bar at room temperature.

After testing for tightness, the stirrer (450 revolutions/minute) and the heating were switched on simultaneously.

The absorption of hydrogen started immediately, the hydrogen pressure falling rapidly and the reaction temperature rising.

After every fall in the hydrogen pressure to 50 bar, hydrogen was forced in again up to 100 bar. The absorption of hydrogen had ended after a reaction time of 5 to 6 minutes and a hydrogen uptake of 160 bar. In order to ensure complete reduction of the 3,4-dichloronitrobenzene, the reaction mixture which had been heated to 100° C. was subsequently stirred at 100° C. for a further 20 minutes under a hydrogen pressure of 100 bar.

The mixture was then cooled to 30° C., while stirring, and the resulting amine solution was filtered off from the catalyst.

The catalyst filtered off can be recycled and employed again for further hydrogenations of 3,4-dichloronitrobenzene by the procedure described above. In the following table, "recyclings 0" means that fresh catalyst was employed, and "recyclings 1 to 3" means that a catalyst which had already been used once, twice or three times in the same reaction and recycled was used. The filtered amine solution was analyzed by HPLC methods in respect of the formation of undesirable by-products.

A series of reactions was carried out in the presence of various hydrogenation catalysts containing, according to the invention, platinum and nickel and/or cobalt and, for comparison, only platinum, in each case on active charcoal supports, in accordance with the procedure described above.

The hydrogenation results obtainable under the same conditions and in the same apparatus are reproducible and can be used to evaluate the catalytic activity and selectivity of the catalysts employed relative to one another.

The results obtained during the laboratory testing are summarized in the following table:

TABLE

| Example | | Catalyst composition | Recyclings | By-products in the amine solution, which contained about 18-19% of DCA | | |
|---|---|---|---|---|---|---|
| | | | | Chloroaniline and aniline [ppm] | TCAB [ppm] | TCAOB [ppm] |
| 2 | | 1% of Pt + 0.1% of Ni/ active charcoal | 0 | 1054 | 8.6 | — |
| | | | 1 | 1039 | 1.0 | — |
| | | | 2 | 699 | 3.2 | — |
| | | | 3 | 549 | 1.4 | — |
| 3 | | 1% of Pt + 0.2% of Ni/ active charcoal | 0 | 1082 | 0.9 | — |
| | | | 1 | 711 | 1.1 | — |
| | | | 2 | 594 | 1.5 | — |
| | | | 3 | 430 | 0.9 | — |
| 4 | | 1% of Pt + 0.3% of Ni/ active charcoal | 0 | 1100 | — | — |
| | | | 1 | 919 | 0.6 | — |
| | | | 2 | 896 | 0.6 | — |
| | | | 3 | 467 | 2.4 | — |
| 5 | | 1% of Pt + 0.5% of Ni/ active charcoal | 0 | 2157 | — | — |
| | | | 1 | 1553 | 0.7 | — |
| | | | 2 | 1444 | 1.3 | — |
| 6 | | 1% of Pt + 1.0% of Ni/ active charcoal | 0 | 2713 | — | — |
| | | | 1 | 2509 | 0.5 | — |
| | | | 2 | 2115 | 0.2 | — |
| | | | 3 | 1266 | 0.3 | — |
| 7 | | 1% of Pt + 0.2% of Co/ active charcoal | 0 | 689 | 41 | — |
| | | | 1 | 461 | 5 | — |
| | | | 2 | 449 | 0.6 | — |
| | | | 3 | 297 | — | — |
| 8 | | 1% of Pt + 1% of Co/ active charcoal | 0 | 562 | 5.9 | — |
| 9 | | 1% of Pt + 0.1% of Ni + 0.1% of Co/active charcoal | 0 | 1224 | 7.2 | — |
| | | | 1 | 1270 | 4.4 | — |
| 10 | | 1% of Pt + 0.2% of Ni + 0.2% of Co/active charcoal | 0 | 1372 | — | — |
| | | | 1 | 1176 | 0.8 | — |
| | | | 2 | 918 | 0.6 | — |
| 11 | | 1% of Pt + 0.5% of Ni + 0.5% of Co/active charcoal | 0 | 1203 | 0.4 | — |
| | | | 1 | 912 | 0.8 | — |
| | | | 2 | 599 | 0.8 | — |
| 12 | for comparison | 1% of Pt on active charcoal | 0 | 3455 | 138 | 2.1 |
| | | | 1 | 1654 | 80 | 0.4 |
| | | | 2 | 827 | 81 | — |
| | | | 3 | 554 | 81 | — |

What is claimed is:

1. In a process for the preparation of a chlorinated aromatic amine by reaction of a chlorinated aromatic nitro compound of the formula

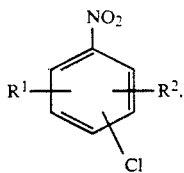 (I)

in which
R$^1$ and R$^2$ are identical or different and each denote hydrogen, methyl or chlorine,
with hydrogen in the presence of a hydrogenation catalyst under pressure, at elevated temperature and in the presence of a solvent and small amounts of a basic compound, the improvement which comprises the basic compound being ammonia, the ammonia being present in amounts of 0.2 to 5% by weight based on the chlorinated aromatic nitro compound employed, the reaction being carried out in the presence of a hydrogenation catalyst selected from the group consisting of platinum, nickel and cobalt on an active charcoal support, platinum and cobalt on an active charcoal support and platinum and nickel on an active charcoal support, and the charcoal support in each case being a porous active charcoal of vegetable or animal origin having a high surface area, thereby obtaining a chlorinated aromatic amine having a low content of by-products of azobenzene and azoxybenzene derivatives.

2. The process of claim 1, in which o-nitrochlorobenzene, m-nitrochlorobenzene, p-nitrochlorobenzene, 2,4-dichloro-nitrobenzene, 2,5-dichloro-nitrobenzene, 3,4-dichloro-nitrobenzene, 2,3,5-trichloro-nitrobenzene, 2,4,6-trichloro-nitrobenzene or 2-chloro-4-nitrotoluene is reacted with hydrogen.

3. The process of claim 1, which is carried out at temperatures in the range from 120° to 160° C. under pressures in the range from 50 to 250 bar.

4. The process of claim 1, in which an aliphatic alcohol having 1 to 8 C atoms is used as the solvent.

5. The process of claim 1, in which an aromatic hydrocarbon having 6 to 10 C atoms is used as solvent.

6. The process of claim 1, in which the catalyst contains 0.3 to 7% by weight of platinum and 1 to 100% by weight of nickel and cobalt, based on platinum.

7. The process of claim 1, in which the catalyst contains platinum and nickel.

* * * * *